United States Patent [19]

McLeod et al.

[11] Patent Number: 5,800,543
[45] Date of Patent: Sep. 1, 1998

[54] ARTIFICIAL LIGAMENT

[75] Inventors: Alan Rory Mor McLeod, Evesham; Ali Shafighian, Hempton, both of Great Britain

[73] Assignee: Surgicraft Limited, Redditch, United Kingdom

[21] Appl. No.: 532,641

[22] PCT Filed: Mar. 31, 1994

[86] PCT No.: PCT/GB94/00678

§ 371 Date: Dec. 13, 1995

§ 102(e) Date: Dec. 13, 1995

[87] PCT Pub. No.: WO94/22395

PCT Pub. Date: Oct. 13, 1994

[30] Foreign Application Priority Data

Mar. 31, 1993 [GB] United Kingdom ............. 9306737

[51] Int. Cl.⁶ ...................................................... A61F 2/08
[52] U.S. Cl. ................................. 623/13; 623/11; 87/7; 87/8; 87/11
[58] Field of Search ......................... 623/11, 13, 66, 623/16, 15; 87/5–8, 11

[56] References Cited

U.S. PATENT DOCUMENTS

| | | | |
|---|---|---|---|
| 4,792,336 | 12/1988 | Hlavacek et al. | 623/13 |
| 4,917,699 | 4/1990 | Chervitz | 623/13 |
| 4,917,700 | 4/1990 | Aikins | 623/13 |
| 4,946,377 | 8/1990 | Kovach | 623/13 |
| 5,049,155 | 9/1991 | Bruchman et al. | 623/17 |
| 5,147,400 | 9/1992 | Kaplan et al. | 623/66 |
| 5,192,322 | 3/1993 | Koch et al. | 623/13 |
| 5,197,983 | 3/1993 | Berman et al. | 623/13 |
| 5,263,984 | 11/1993 | Li et al. | 623/13 |

FOREIGN PATENT DOCUMENTS 9011735  10/1990  WIPO ............................... 623/13

*Primary Examiner*—Michael J. Milano
*Assistant Examiner*—Tram Anh T. Nguyen
*Attorney, Agent, or Firm*—Trexler, Bushnell, Giangiorgi & Blackstone, Ltd.

[57] ABSTRACT

A method of manufacturing an artificial ligament device, which may be a ligament augmentation device, a delivery device for an autologous graft, or a prosthetic ligament, comprises securing a plurality of tows of biocompatible material side-by-side in a flat elongate array, as by light braiding, looping the tows back at one end of the device to form an eye with the tows grouped together around the eye, and applying whipping around the grouped tows around the eye.

16 Claims, 3 Drawing Sheets

ARTIFICIAL LIGAMENT

BACKGROUND OF THE INVENTION

Field of the Invention

This invention relates to artificial ligament devices, e.g., ligament augmentation devices such as are used for reinforcing or supplementing damaged ligaments while healing takes place or for use in conjunction with autologous grafts for reconstructing torn ligaments, or artificial ligaments per se, or delivery devices for autologus grafts.

SUMMARY OF THE INVENTION

An object of the invention is to provide artificial ligament devices each having a strong integral eye at one or both ends for attachment of a pulling cord or wire and/or for fitting round an anchor member for securing to a bone.

Another object is to provide ligament augmentation devices suitable for reinforcing or supplementing damaged ligaments while healing takes place but also adapted for use in conjunction with autologous grafts for reconstructing torn ligaments.

According to the present invention, a method of manufacturing an artificial ligament device comprises securing a plurality of tows of biocompatible material side-by-side in a flat elongate array, looping the tows back at one end of the device to form an eye with the tows grouped together round the eye, and applying whipping round the grouped tows around the eye.

The combination of grouping the tows together round the eye and applying whipping round the grouped tows round the eye results in a strong integral eye for attachment of a pulling cord or wire and/or for secure fixing of that end of the device by fitting the eye round an anchor member secured to a bone.

When looping back to form the eye the array of tows may be twisted through 180°, or any multiple thereof, to effect the grouping together of the tows round the eye, or the array of tows may simply be rolled together round the eye as whipping progresses.

The eye may be formed by grouping the tows together between a main flat length of the array of tows and a short flat length, the short length being stitched to the main length after forming the eye with twisting through 180°, or a multiple thereof. Alternatively, the eye may be formed by grouping the tows together between two similar lengths of the flat array of tows, with or without twisting of the grouped tows through 180°, or a multiple thereof, and the similar flat lengths are sewn together edge-to-edge at least part way along their mutual length, thus forming a device having an overall width twice that of the initial flat array of tows.

The width of the initial flat array of tows, or the overall width of lengths sewn together edge-to-edge (as just described above), may be such as can be wrapped round an autologous graft and the mating edge of the array, or combined arrays, stitched together to form a sleeve enclosing the autologous graft or one end thereof, whereby the artificial ligament device can also serve as a delivery device for the autologous graft.

Alternatively, the initial flat array of tows, or combined arrays sewn together edge to edge (as described above) may be such as to give a bimodal form, being either opened or compacted. When in the opened form, the overall width may be such as can be wrapped around an autologous graft and the mating edges of the array, or combined arrays, stitched together to form a sleeve enclosing the autologous graft. When in the rolled, compacted form, the overall bulk may be such as can be enclosed within the overall cross-section of an autologous graft. A trimodal form may be manufactured, to afford an even greater combined width, by sewing an additional array of tows between the lengths extending from the eye.

However, any device within the scope of this invention can be used simply as a ligament augmentation device by fitting its eye round an anchor member for securing to a bone, the other end, or divided ends, being secured by suturing to tissue or by another anchor member or staples to another bone.

Each tow may be formed of a multiplicity of polyester (or similar biocompatible or bioabsorbable) filaments and the tows secured together by light braiding, to form the flat array. The array (or parts thereof) may be treated with a biocompatible, bioabsorbable or pharmacologically active coating.

The invention also comprises artificial ligament devices manufactured by any method as described above, including such devices wrapped round autologous grafts and enclosed in suitable sealed packaging.

Methods of manufacturing artificial ligament devices in accordance with the invention and artificial ligament devices manufactured thereby and their uses will now be described, by way of example only, with reference to the accompanying drawings.

DESCRIPTION OF THE PREFERRED EMBODIMENTS OF THE INVENTION

Figure 1:
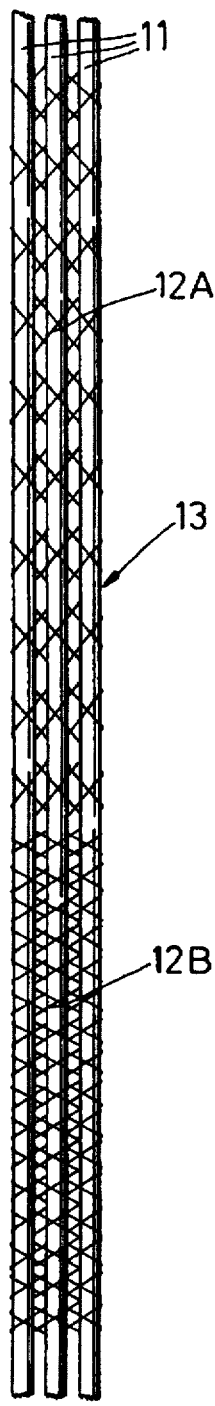
FIG. 1 is a diagrammatic fragmentary elevation of an array of tows for use in a preferred method according to the invention, shown twice actual size.
Figure 6:
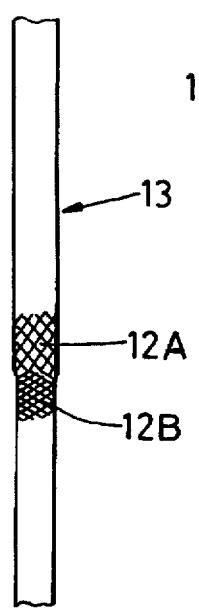
FIG. 6 corresponds to FIG. 1 but shown actual size and illustrating the diagrammatic representation of the transition from loose braiding to tight braiding used where appropriate in the following drawings.

In FIG. 1 three tows 11 of biocompatible material, e.g., a multiplicity of polyester filaments are secured together by light braiding either loose braiding 12A or tight braiding 12B (see also FIGS. 6 and 7), side-by-side in a flat elongate array 13.

Figure 3:
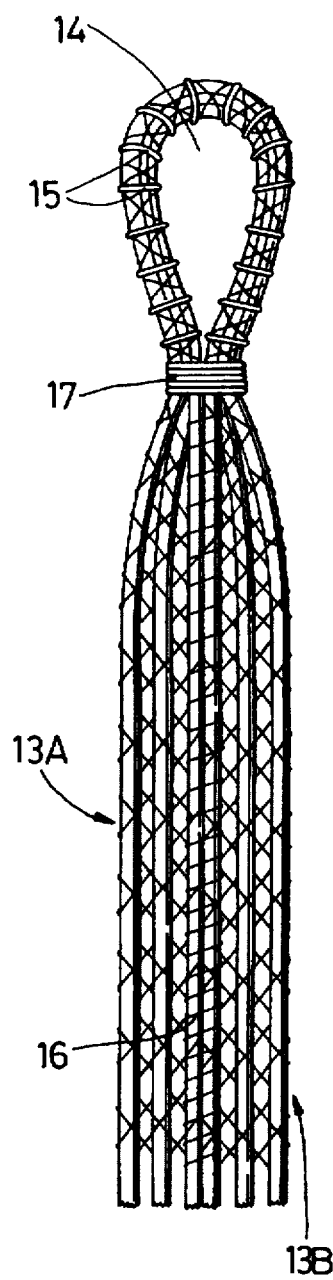
FIG. 3 is a similar elevation to FIG. 2 illustrating further steps in the preferred method.
Figure 5:
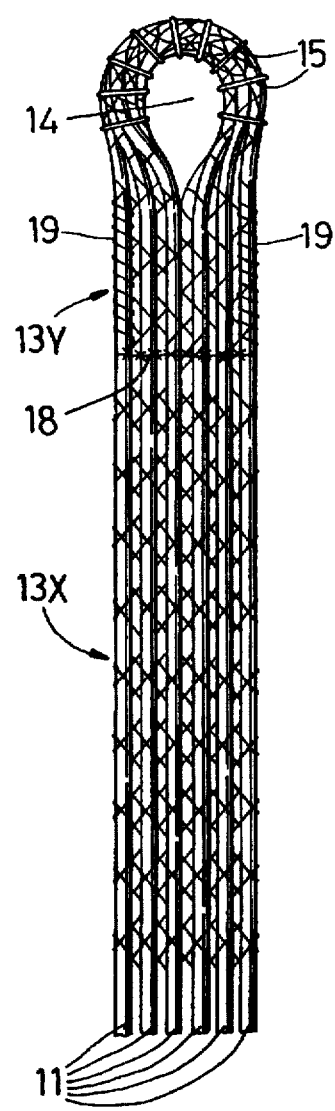
FIG. 5 is a similar elevation to FIG. 3 but illustrates an alternative method of manufacturing an artificial ligament device in accordance with the invention.

To form an eye 14 at one end of an artificial ligament device (see FIGS. 7 to 10) in accordance with the invention, the tows are looped back at one end of the device, with the tows grouped together round the eye and whipping 15 applied round the eye, as shown in FIGS. 3 and 5.

Figure 4:
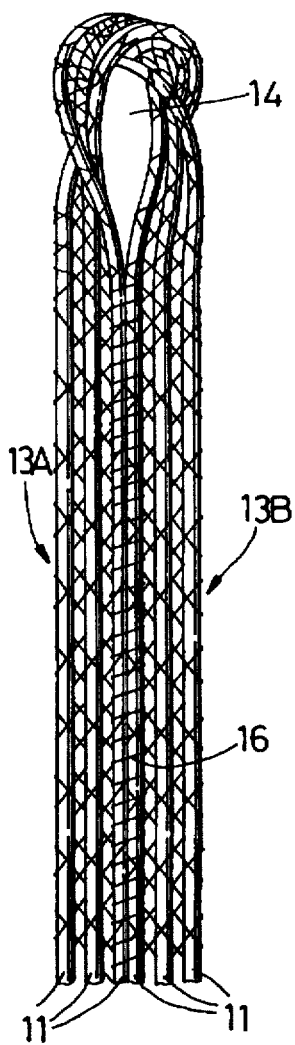
FIG. 4 corresponds to FIG. 2 but illustrates a modification in the preferred method.

When looping back to form the eye 14 the array 13 of tows 11 may be twisted through 180°, as shown in FIG. 4, or any multiple thereof.

Figure 2:
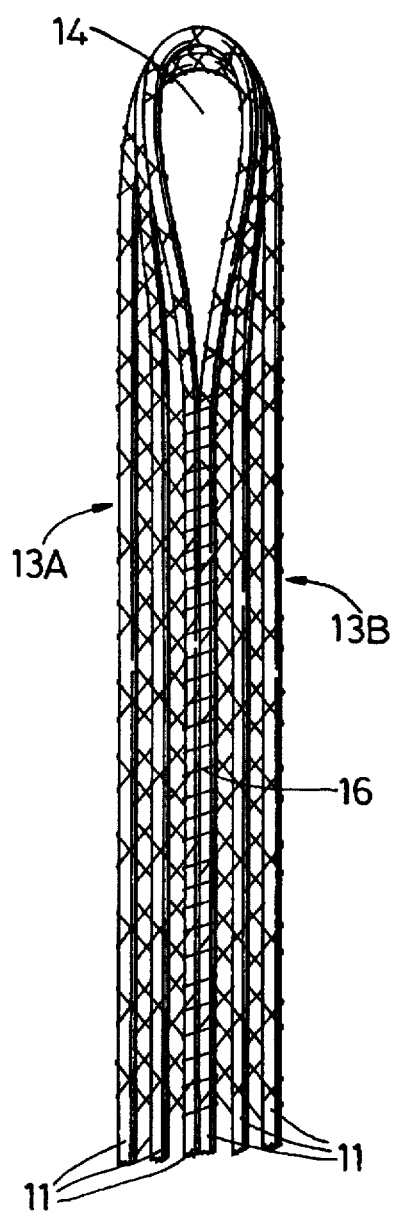
FIG. 2 is a fragmentary elevation illustrating initial steps in the preferred method using an array of tows as in the upper part of FIG. 1.
Figure 7:
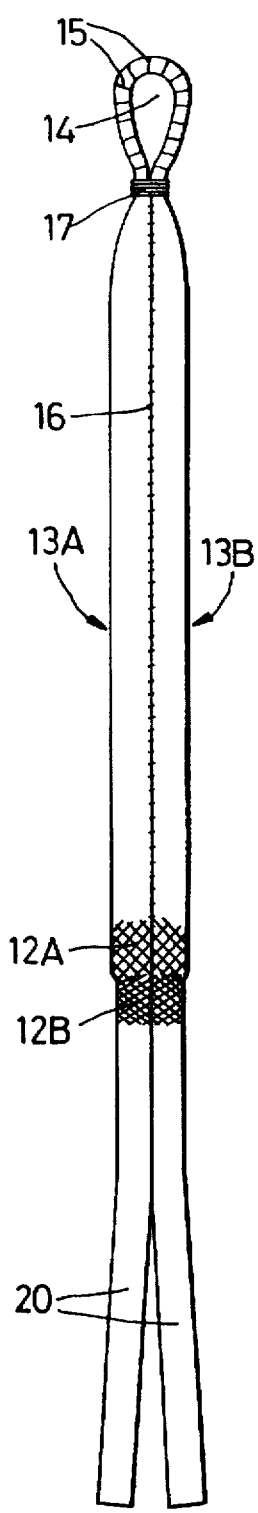
FIG. 7 shows a ligament augmentation device manufactured by the preferred method of the invention.
Figure 9:
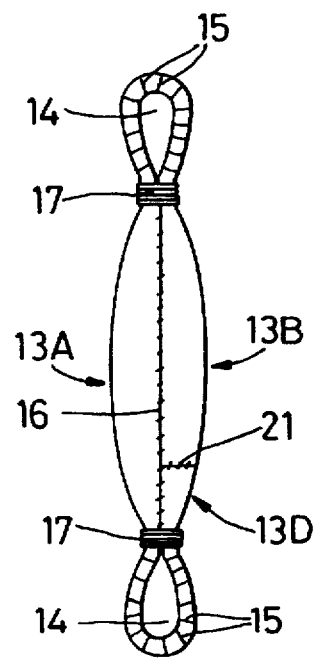
FIG. 9 shows a device in accordance with the invention provided with an eye at each end.

In FIGS. 2 and 3, and also in FIGS. 4, 7 and 9, the eye 14 is formed by grouping the tows 11 between two similar lengths 13A, 13B of the flat array 13 of tows, and the similar flat lengths are sewn together edge-to-edge at least part way along their mutual length (see particularly FIG. 7) by stitching 16, thus forming a device having an overall width twice that of the initial array 13 of tows 11. In FIG. 3 a lashing 17 is applied around the base of the eye 14 to relieve the stitching 16 of any damaging stress.

In FIG. 5, the eye 14 is formed by grouping six tows 11 between a main flat length 13X of the array of tows and a short flat length 13Y, the short length being stitched to the main length, across the end 18 of the short length and along its sides 19 after forming the eye with twisting through 180° (or a multiple thereof). The short length 13Y is indicated as having loose braiding securing the tows 11 together, similar to the braiding along the main length 13X, but tight braiding may be used advantageously in the short length to afford greater stiffness all around the eye.

The artificial ligament device shown in FIG. 7 has divided ends 20 which may be secured by suturing to tissue or by an anchor member or staples to a bone.

Figure 8:
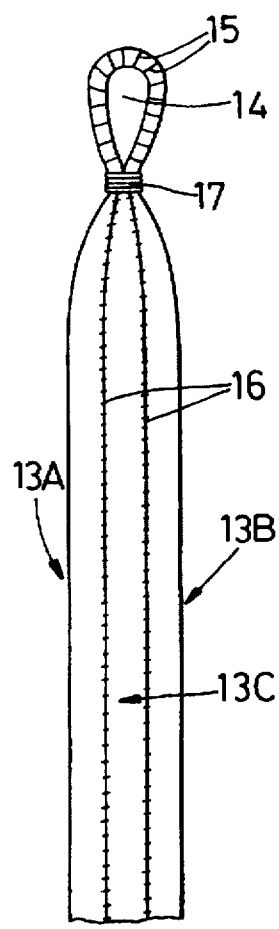
FIG. 8 shows a trimodal form of device in accordance with the invention.

The device shown in FIG. 8 has a trimodal form, to afford an even greater combined width, by sewing an additional array 13C of tows between the lengths 13A, 13B extending from the eye 14.

The device shown in FIG. 9 has an eye 14 at each end, the eye at one end being formed between lengths 13A and 13B, while the eye at the other end is formed between the length 13A and a return portion 13D with stitching 21 between the adjoining ends of the length 13B and the return portion.

Figure 10:
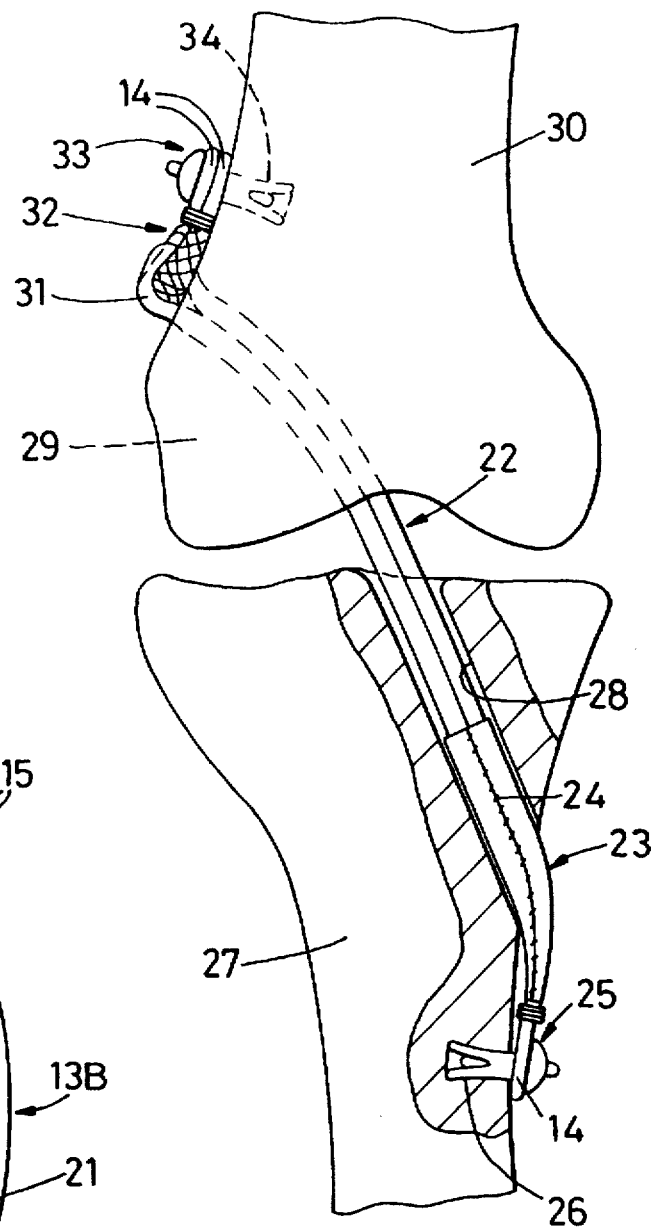
FIG. 10 is a diagrammatic illustration of a knee showing devices as in FIGS. 8 and 9 in use to secure an autologous graft.

In FIG. 10, an autologous graft 22 is doubled back on itself and its two ends wrapped in a device 23 in accordance with the invention having an adequate width such as the device shown in FIG. 8, to form a sleeve, the mating edges of which are shown stitched at 24 and the device 23 also being stitched to the autologous graft. The eye 14 of the device 23 is shown fitted round an anchor member 25, e.g., as in U.K. Patent GB 2 084 468B, secured in a hole 26 in a tibia 27, and the augologous graft 22 extends through a tunnel 28 in the tibia, then across the condylar notch 29 of the femur 30, to which the loop 31 of the graft is secured by a sling 32, such as may be formed by the device of FIG. 9, doubled through the loop of the graft and having its eye 14 fitted round another anchor member 33 (similar to the anchor member 25) secured in a hole 34 in the femur.

We claim:

1. A method of manufacturing an artificial ligament device comprising securing a plurality of tows of biocompatible material side-by-side in a flat elongate array by braiding, looping the tows back at one end of the device to form an eye, securing the flat lengths adjoining the eye to each other side-by-side by stitching, grouping the tows together around the eye, applying whipping around the grouped tows around the eye, and applying lashing around a base of the eye.

2. A method as in claim 1, wherein when looping back to form the eye the array of tows is twisted through 180°, to effect the grouping together of the tows round the eye.

3. A method as in claim 1, wherein the array of tows forming the eye are rolled together into a circular cross-section around the eye.

4. A method as in claim 1, wherein the similar flat lengths adjoining the eye are sewn together edge-to-edge part way along their mutual length, thus forming a device having divided ends.

5. A method as in claim 1, wherein the overall width of the flat lengths adjoining the eye are wrapped around an autologous graft and the resultant mating edges of the array are stitched together to form a sleeve enclosing at least one end portion of the autologous graft.

6. A method of claim 1, wherein a trimodal form is manufactured by sewing an additional array of tows between the lengths extending from the eye.

7. A method as in claim 1, wherein each tow is formed of a multiplicity of polyester filaments and the tows are secured together by light braiding to form the flat array.

8. A method as in claim 1, wherein the array is treated with a bioabsorbable or pharmacologically active coating.

9. A method as in claim 1, wherein an other eye is provided at the other end of the device by looping the tows at one side of the device back again, securing the flat lengths adjoining the other eye to each other side-by-side by stitching, grouping the tows together around the other eye, applying whipping around the grouped tows around the other eye, applying lashing around a base of the other eye, and stitching mating ends of the array to each other intermediate the eyes at the other side of the device.

10. An artificial ligament device comprising a plurality of tows of biocompatible material secured side-by-side in a flat elongate array by braiding, the tows being looped back at one end of the device to form an eye, the flat lengths adjoining the eye being secured to each other side-by-side by stitching, the tows around the eye being grouped together and whipped, and lashing being applied around a base of the eye.

11. A device in claim 10, wherein the array of tows is twisted through 180° while forming the eye.

12. A device as in claim 10, wherein the tows forming the eye are rolled together into a circular cross-section around the eye.

13. A device as in claim 10, wherein the flat lengths adjoining the eye are sewn together part way along their mutual length, thus providing divided ends to the device.

14. A device as in claim 10, wherein the overall width of the flat lengths adjoining the eye enables them to be wrapped around an autologous graft and have their resultant mating edges stitched together.

15. A device as in claim 10, having a trimodal form created by sewing an additional array of tows between the lengths adjoining the eye.

16. A device as in claim 10 wherein the tows are looped back at one side of the device and back again to form an other eye, the tows around the other eye being grouped together and whipped, lashing being applied around a base of the other eye, mating ends of the array being stitched to each other, and the flat lengths with those mating ends being stitched edge-to-edge to the flat length at the other side of the device.

* * * * *